United States Patent
Lui et al.

(10) Patent No.: US 9,919,916 B2
(45) Date of Patent: Mar. 20, 2018

(54) MANUFACTURE OF MICRONEEDLES

(71) Applicant: Semitechnologies Limited, Swansea (GB)

(72) Inventors: Yufei Lui, Swansea (GB); Owen Guy, Swansea (GB)

(73) Assignee: Semitechnologies Llimited, Swansea (GB)

( * ) Notice: Subject to any disclaimer, the term of this patent is extended or adjusted under 35 U.S.C. 154(b) by 0 days.

(21) Appl. No.: 15/031,957

(22) PCT Filed: Oct. 15, 2014

(86) PCT No.: PCT/GB2014/000415
§ 371 (c)(1),
(2) Date: Apr. 25, 2016

(87) PCT Pub. No.: WO2015/059437
PCT Pub. Date: Apr. 30, 2015

(65) Prior Publication Data
US 2016/0264408 A1 Sep. 15, 2016

(30) Foreign Application Priority Data
Oct. 23, 2013 (GB) .................................. 1318700.0

(51) Int. Cl.
*B44C 1/22* (2006.01)
*C25F 3/00* (2006.01)
(Continued)

(52) U.S. Cl.
CPC ..... *B81C 1/00111* (2013.01); *A61M 37/0015* (2013.01); *A61M 2037/003* (2013.01); *A61M 2037/0053* (2013.01); *B81B 2201/055* (2013.01); *B81C 2201/0132* (2013.01); *B81C 2201/0133* (2013.01); *B81C 2201/0159* (2013.01); *B81C 2201/0176* (2013.01); *B81C 2201/0181* (2013.01); *C23C 16/402* (2013.01)

(58) Field of Classification Search
USPC .......................................................... 216/11
See application file for complete search history.

(56) References Cited

U.S. PATENT DOCUMENTS

| 5,855,801 | A | 1/1999 | Lin et al. |
| 6,815,360 | B1 * | 11/2004 | Canham .............. B81C 1/00087 438/706 |

(Continued)

FOREIGN PATENT DOCUMENTS

CN 101244303 A 8/2008

OTHER PUBLICATIONS

Liu, Yufei et al., "Advanced deep reactive-ion etching technology for hollow microneedles for transdermal blood sampling and drug delivery," *IET Nanobiotechnology, The Institution of Engineering and Technology*, vol. 7, No. 2, Jun. 1, 2013, pp. 59-62.

*Primary Examiner* — Roberts Culbert
(74) *Attorney, Agent, or Firm* — Dinsmore & Shohl LLP

(57) ABSTRACT

A method of forming microneedles where through a series of coating and etching processes microneedles are formed from a surface as an array. The microneedles have a bevelled end and bore which are formed as part of the process with no need to use a post manufacturing process to finish the microneedle.

19 Claims, 4 Drawing Sheets a)

b)

(51) Int. Cl.
*B81C 1/00* (2006.01)
*A61M 37/00* (2006.01)
*C23C 16/40* (2006.01)

(56) References Cited

U.S. PATENT DOCUMENTS

| | | |
|---|---|---|
| 2002/0082543 A1* | 6/2002 | Park .................... A61B 5/1411 604/21 |
| 2006/0172541 A1 | 8/2006 | Lee |
| 2009/0093776 A1 | 4/2009 | Yue et al. |

* cited by examiner a)

b)

MANUFACTURE OF MICRONEEDLES

CROSS REFERENCE TO RELATED APPLICATIONS

This application is the U.S. National Phase of international patent application Serial No. PCT/GB2014/000415, filed Oct. 15, 2014, which claims the benefit of international application Serial No. GB 1318700.0, filed Oct. 23, 2013, the contents of both of which are incorporated herein in their entirety.

FIELD OF THE INVENTION

The invention relates to the manufacture of microneedles, otherwise known as microstructure needles and in particular but not exclusively microneedles made from materials such as silicon.

BACKGROUND OF THE INVENTION

It is well known that the delivery of materials to the body can be via syringes and hypodermic needles but such devices are generally used to deliver a relatively large amount of material at a defined point in time as a single dose. More recently the medical profession has seen the advantage of delivering a smaller amount of material over a time period and to do this transdermal delivery devices have been developed which have an array of microneedles that are in contact with the skin. The microneedles deliver a small amount of material over a period of time and to do this the microneedles have smaller diameters and sharper tips than conventional needles in order to minimize pain and damage to the skin. The microneedles could also be used for blood and cell sampling.

Microneedles have been fabricated from a range of materials including metals, silicon, silicon dioxide, polymers and glass. The mechanism for drug delivery using microneedles is not based on diffusion as is the case in traditional hypodermic delivery but on the mechanical disruption of the skin and the placement of the drug within the epidermis which has capillaries that can then take up the drug and deliver it to the site of action in the body. The microneedles have a length of from a few hundred micrometers to a few millimeters so that they only penetrate the superficial layers of the skin where the density of nerve receptors is low and consequently the use of microneedles is perceived as a being a painless way of delivering drugs, vaccines, and/or cells.

Microneedles are generally produced from a substrate and in the case of silicon needles the needles are produced from wafer of silicon. Thousands of needles can be fabricated on a single wafer and this leads to the production of needles with a high degree of reliability and accuracy.

It is known to fabricate silicon microneedles with flat tips by dry etching technologies using various gas compositions and processes. However, dry etching processes are expensive, and the process does suffer from some drawbacks including for example the requirement for specialised equipment operated by highly trained personnel. Also, batch processing is generally not possible as usually only one wafer can be treated at a time.

U.S. Pat. No. 5,855,801 describes a wet etch process using hydrofluoric acid for fabricating microneedles by providing a substrate, depositing an un-etchable membrane over the substrate, and opening etching holes in the membrane layer to allow flow of etchant underneath to form a cavity and provide a desired needle shape.

However both processes have the disadvantage that if a dry etch method if used then a high level of control is needed to obtain consistency and uniformity in the shape of the needles that are produced, which make the process expensive. In the case of wet etch processes again because the etching process cuts across several crystal planes of the material that is being etched then precise control of the process is needed which may not be compatible with the dry etch processes.

The invention seeks to overcome the prior art by providing an improved process for fabricating microstructures in a consistent and cost effective way.

SUMMARY OF THE INVENTION

According to the present invention, there is provided a method of manufacturing a microneedle having a stem and a beveled end, the process comprising:

providing a semiconductor bulk material having a first and a second face which are parallel to one another, depositing a barrier layer on said first and second faces with;

coating first and second faces with a photolithography sensitive layer, removing areas of the photolithography sensitive and barrier layer on the first face to form windows between areas of barrier layer, wherein the windows are exposed to an wet etching process so part of the semiconductor bulk material is removed from the first face until a cavity is formed having at least one side wall extending at an oblique angle to the first face and towards the second face of the semiconductor bulk material, coating the at least one side wall of the cavity with a coating layer, forming at channel by a dry etching, through the second face of the bulk material towards the coating layer of the cavity so the channel meets the coating layer which provides a cap for the channel as well as areas of the at least one side wall that border the channel, removing the semiconductor bulk layer from either side of the cap to leave a capped tube extending from the second face extending from as remaining layer of the semiconductor bulk material and removing the cap to form at least one microneedle formed as a stem and beveled end.

Preferably the semiconductor bulk layer is a silicon based material.

Preferably the barrier layer is an oxide.

It is envisaged that the oxide is silicon dioxide.

It is envisaged that the oxide is formed by thermal growth and/or Plasma Enhanced Chemical Vapour Deposition (PECVD).

It is preferred that the first face has a barrier layer that is then coated with a photoresist in discrete locations on the barrier layer.

It is envisaged that areas of the barrier layer that are free of photoresist are subjected to a wet etch process to form one or more cavities in the first face of the semiconductor bulk material.

It is preferred that the wet etching is a potassium hydroxide wet etch process.

Preferably the coating layer on the at least on side wall of the cavity is laid down by physical vapour deposition (PVD) and/or plasma enhanced chemical vapour deposition (PECVD) process.

Alternatively the coating layer on the at least one side wall of the cavity is laid down by a photolithographic process.

It is envisaged that the photolithographic process includes spray coating and photolithography.

It is envisaged that semiconductor bulk material that is either side of the cap is removed using a further wet etch process.

It is preferred that the further wet etch process uses a solution of buffered halide, preferably hydrogen fluoride (HF).

It is envisaged that the dry etch process to form the channels is deep reactive-ion etching (DRIE).

According to a further aspect of the invention there is provided one or more beveled microneedles formed by a process according to a first aspect of the invention.

The process used allows for the production of microneedles having particularly smooth surfaces. The smooth surfaces are themselves also highly advantageous for the medical device applications, as the problem of removal of skin cells is avoided, and hence there is a much improved confidence in the extent of drug delivery. This is particularly important in the example of delivering for example vaccines to specific cell regions within the skin. Dry etched needles have a roughened surface which needs smoothening by additional post-fabrication processing in order to reduce needle occlusion by tissue/debris. The smooth wet etched needles of our process do not retain tissue on their surfaces on withdrawal from skin or other target tissue after insertion into same.

The process is particularly suited to fabricating an array of upright out-of-plane needles; and wherein the process simultaneously fabricates a plurality of arrays of needles where the plurality of needles are fabricated on a semiconductor wafer. This process leads to a very efficient process with high production reliability. By fabricating the beveled microneedle on different panels created via the wet etching process, the injection flow could be controlled to flow to different directions, which will increase the efficiency of the injection of drugs, vaccines, and/or cells.

BRIEF DESCRIPTION OF THE DRAWINGS

The present invention will now be more particularly described, by way of example only, with reference to the accompanying drawings, in which.

DETAILED DESCRIPTION OF THE INVENTION

A method based on wet etching produces high-precision microneedles in an upright, out-of-plane, "bed of nails" array, or it may also be used to produce a single needle configuration. The needles that are produced can be used in a range of applications including, but not limited to, medical devices. The description below describes fabrication of hollow needles where a wet etch process is used to produce a bevelled end of the microneedle while dry etching is used to produce the bore of the needle and it is this unusual combination of techniques that allows for efficient production of needles where there is precise process control over microneedle fabrication.

Figure 1:
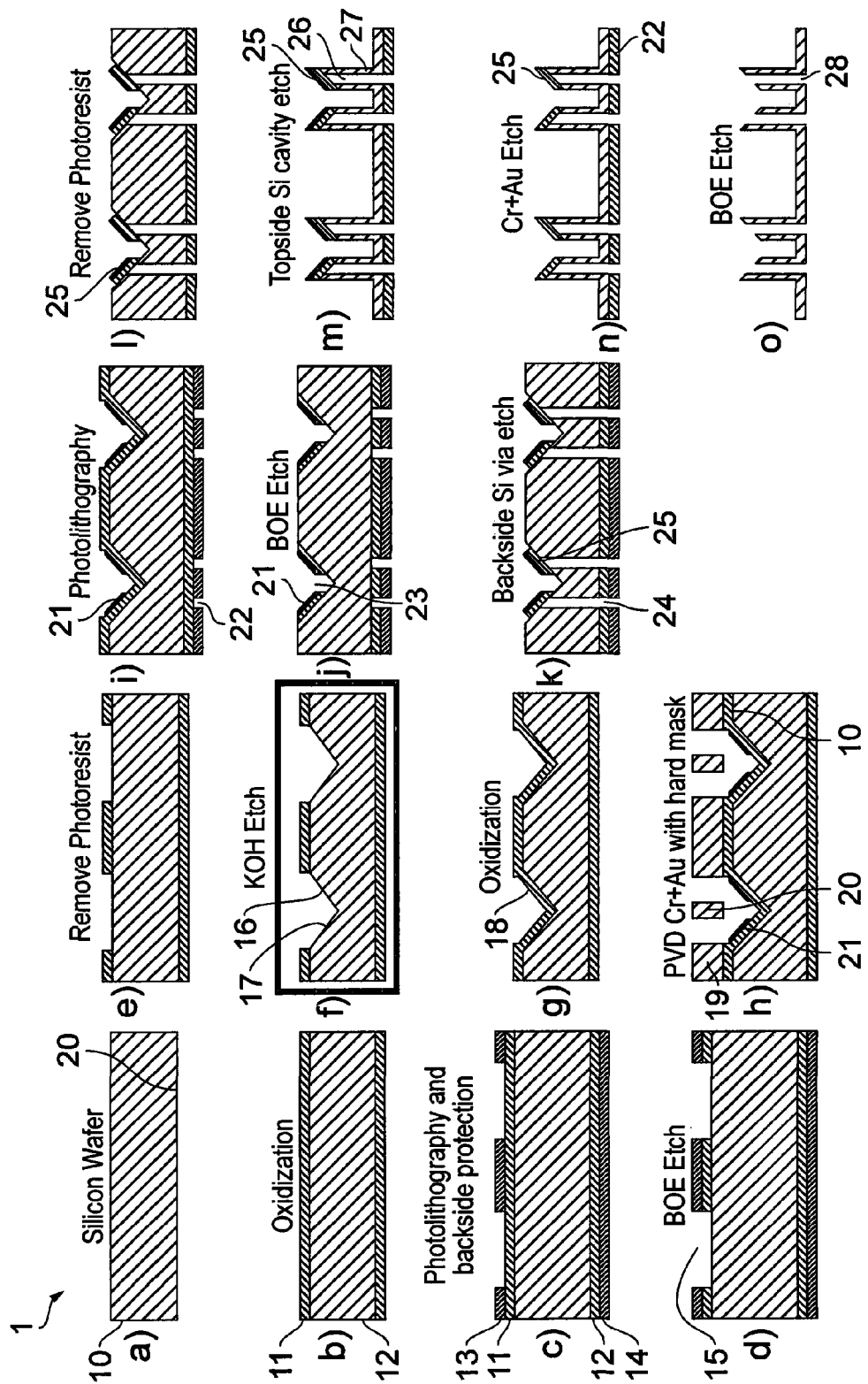
FIG. 1 shows a flow diagram of a process according to a first embodiment of the invention.

As shown in FIG. 1, there is provided a semiconductor bulk material such as silicon which is generally shown as 1 having a first face 10 and a second face 20. Typically the silicon is provided as a wafer with a thickness of around 1000 microns. The opposed surfaces 10, 20 of the silicon wafer are each coated with a protective barrier layer 11 (on the first face) and 12 on the second face) which is typically a oxide layer that is formed by thermal oxide growth or plasma-enhanced chemical vapor deposition (PECVD) using a silicon dioxide so that a layer of about 2 microns is formed on the two opposed faces of the silicon wafer.

A pattern area of photoresist 13 is formed by photolithography over the barrier layer 11 on the first face 10 of the wafer, while a complete layer of photoresist 14 is formed on the barrier layer 12 on the second face of the wafer, otherwise called the backside layer—shown in step c).

Areas of the protective layer that are not covered by the photoresist are removed using an etch process such as a buffered oxide etchant (BOE, a buffered HF solution) to reveal selected 15 areas on the surface of the wafer—step d) and then the photoresist material 13 that remains on the barrier layer on the first face is removed and this is shown in step e). In step f) there is a potassium oxide etch (KOH) to remove areas of the silicon wafer from the first face 10 to form cavities 16 in the first surface of the wafer. An etchant such a hydroxide e.g. potassium hydroxide is very aggressive and hence, the etching extent (time) has heretofore been difficult to accurately control in order to achieve the microstructures of the desired dimensions, particularly height. Therefore such an etchant has not been successfully used heretofore to the knowledge of the inventors to achieve reliable and reproducible fabrication of microstructures such as microneedles of accurately controlled height but this combined with the following dry etching in a material such as silicon allows for more accurate etching by controlling the etching behaviour across the many involved crystal planes in the substrate. The etching process proceeds until a process stopping point when a needle tip is correctly formed as desired. The third stage is stopped to take key dimensional measurements that are desired for the needles. The process can be controlled by using a series of stop and start processes taking measurements at each stage. The wet etch time will be balanced based on the dimensions of the photoresist opening and process temperature.

A negatively sloped inverted pyramid structure exists atop the desired microneedle. Measurements confirm that the negative slope region exists throughout the process. The height of this inverted needle is approximately 100-500 micron and the width of the top is about a few hundred micron. The inverted pyramid structure is separated when the 8 crystal planes form the needle tip. There is also a continuous and sometimes dramatic shift in crystal planes in the semiconductor bulk material and in plane etch as the wet etch process progresses and so the wet etch process, being an aggressive process needs to be controlled. The needle dimensions are controlled via photolithography process, such as diameter of needle hollow from 50 micron to 150 micron, diameter of the whole needle from 150 micron to 300 micron. The sharpness of the needle depends on the angle between the panels such as 54.7 degree between silicon 100 and silicon 111 panels. The wet etch rate will be controlled based on the KOH concentration and process temperature.

Each cavity has at least one side 17 that is at an oblique angle to the first face 10 of the wafer material. As shown the cavities are generally V shaped with an apex of the V pointing towards the second face of the wafer.

The oblique sides 17 are coated with a protective layer 18—see step g) resulting in the whole upper surface of the wafer being coated with a protective layer. As shown in step h) a mask is placed above the coated upper surface 10 of wafer and the mask has an area that is placed above the position on the wafer where the apex of the cavity is and there is a further coating using a physical vapour deposition step with metals and/or alloys, such as Chromium and Gold, to forms an extra layer 21 which forms a coating layer in a mid region of the oblique surface.

There is then a photolithographic step as shown in i) where the backside 20 of the wafer is coated with a resist having apertures 22 in selected areas which extend towards the second face 20 of the wafer. In step j) the front face of the wafer is etched to remove material in proximity to the apex of the cavity to reveal a portion 23 of the surface of the semiconductor bulk material and coating material 21 remains on the oblique surface. There is then a dry etch process starting from the apertures 22 on the backside of the wafer and the etch forms a linear channel 24 through the wafer to the oblique surface where there is the remaining coating material which forms a cap 25 at the end of the channel. In step l) the photoresist from the backside of the wafer is removed. There is then in step m) removal of the semiconductor bulk material by a topside etch process, typically a topside silicon cavity etch to reveal tubes 27 that are upstanding from what would have been a layer that formed face 20 of the wafer. In step n) there is removal of the cap 25 and the photoresist 22 to leave the final microneedles 28 that are held singularly or as an array on a remaining layer that would have formed the second face 20.

Figure 2:
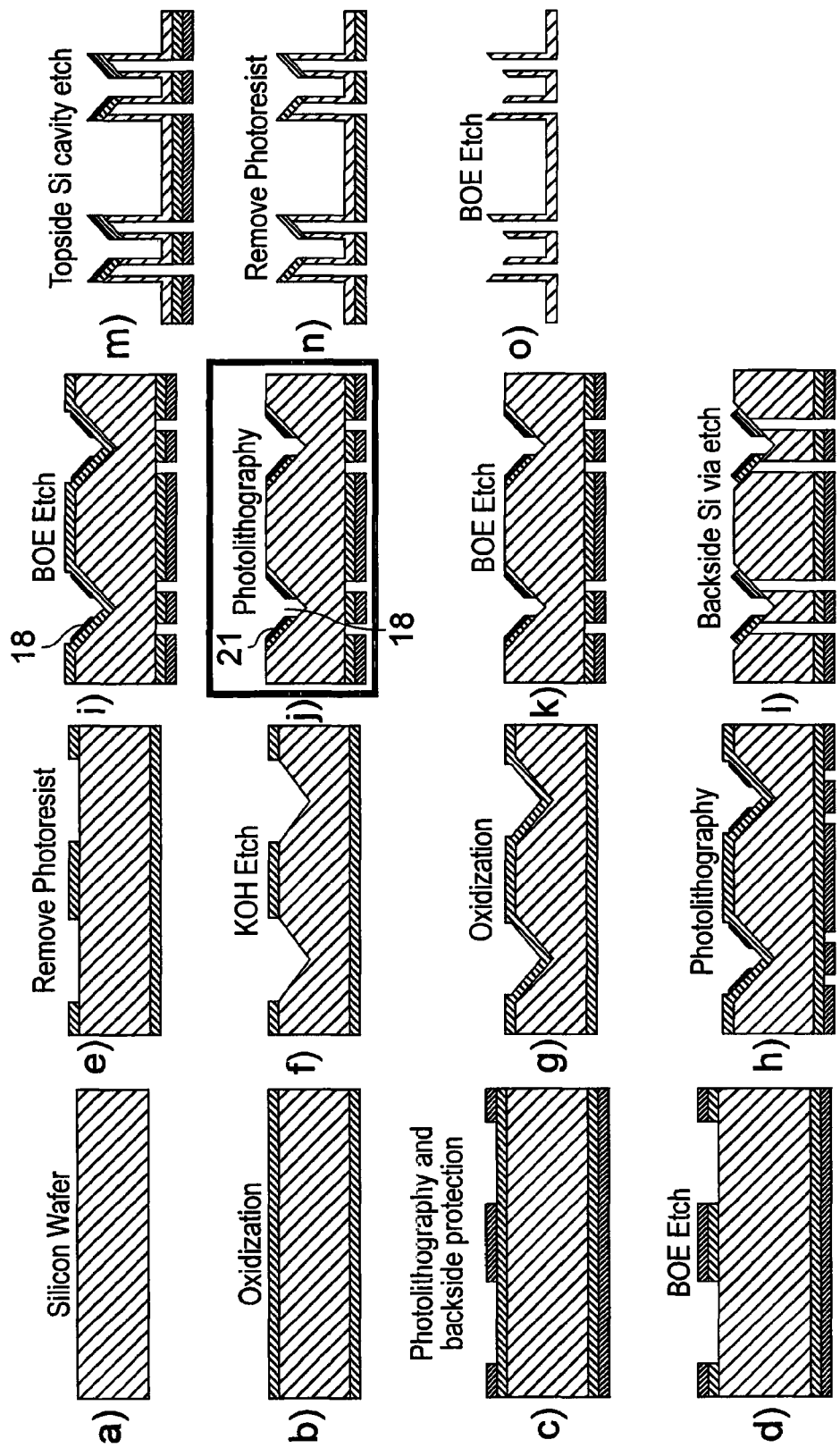
FIG. 2 shows a flow diagram according to a second embodiment of the invention.

FIG. 2 shows a similar process where steps a to g are in the same sequence steps as those shown in the process of FIG. 1. The step that would have been step h) in FIG. 1 has been omitted and instead at step h), there is a photolithography step which is equivalent to step i) in the process shown in FIG. 1 followed by the wet etch using a buffered oxide etch. Rather than using a physical vapour deposition step as was used in the previously described process, a coating layer is formed over the protective layer in order to provide a thickened layer in a particular region of the oblique surface, such as using spray coating and photolithography processes. From then on similar steps to those that were carried out in steps j to o of FIG. 1 are carried out.

Figure 3:
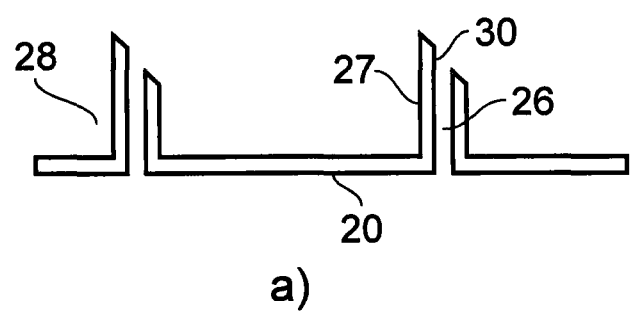
FIG. 3 shows microneedles having bevels in varying directions.
Figure 3:
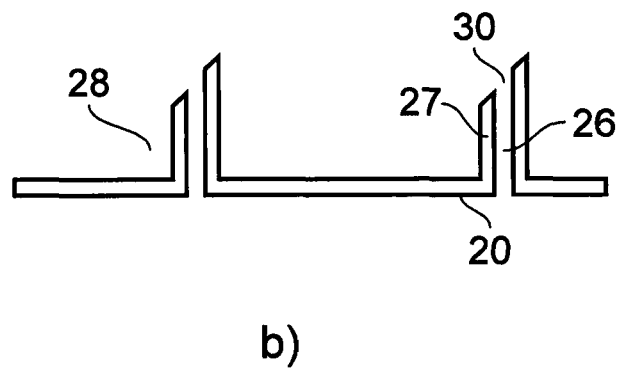

In FIGS. 1 and 2 pairs of needles are formed at the same time because a V shaped cavity is formed in the first face of the semiconductor bulk material with each bevel being formed out of each oblique surface that makes the v shaped cavity. This means that the bevels are orientated towards one another. It in may be that single needles are formed at a cavity and to do this, the cavity may have one face that is at right angles to the first face 10 and one face that is at an oblique angle to the first face. This means that bevels that are in the same orientation as shown in FIGS. 3a and 3b are formed with the tubes extending from a layer that formed the second face 20, with sides of the tubes extending from the surface 20. The bore 26 runs through the length of the tubes and end at a beveled end 30 of the tube so form the microneedle array generally shown as 28.

Figure 4:
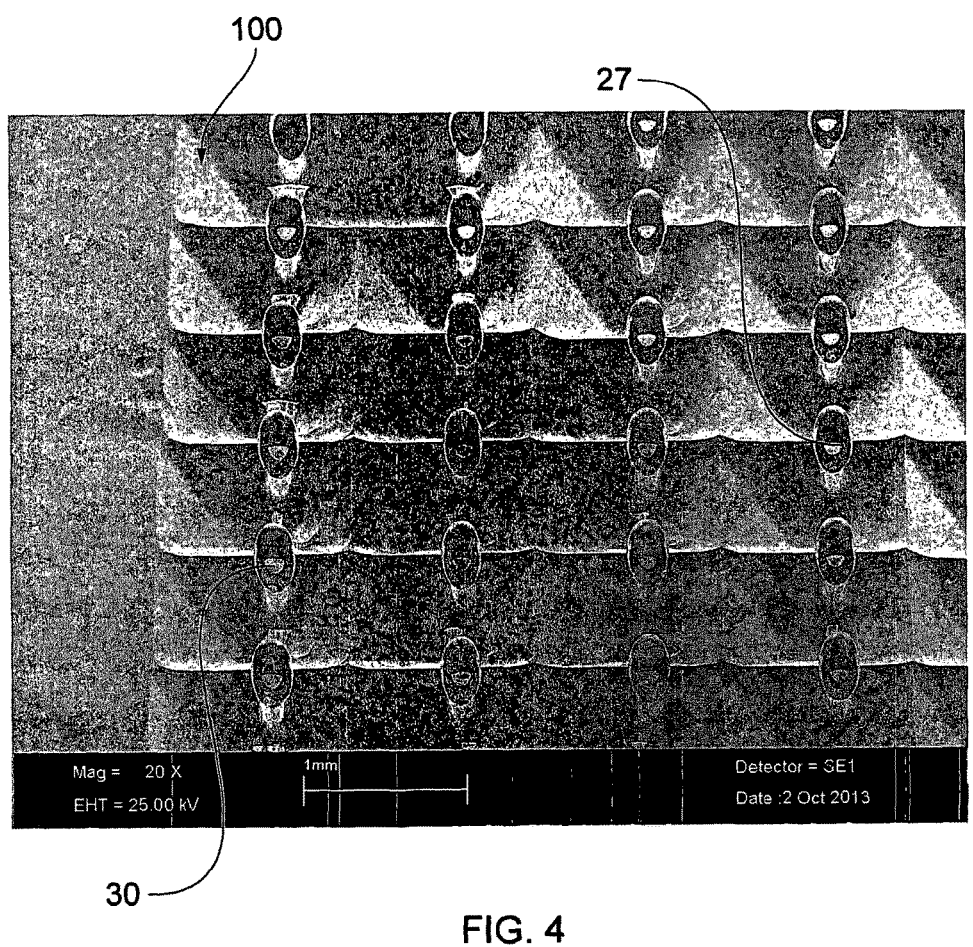
FIG. 4 shows an SEM image of an array of fabricated microneedles.

Finally FIG. 4 shows a scanning electron micrograph (SEM) of an array of microneedles that is generally shown as 100. The mouths 30 of the microneedles are in a regular array and are generally elliptical with the tube 27 forming the length of the microneedle bordering the mouths 30. As can be seen the process allows for the manufacture of a number of microneedles in a regular array making the manufacturing process very efficient with little wastage.

As a result of using the two processes in combination it is possible to achieve accurate prediction of the etch time endpoint so that microneedles of an exactly required height, shape, sharpness and surface quality can be made. The process can be implemented in a batch, the batch including for example up to 25 wafers, each having for example 100 chips, and each chip having for example between tens and hundreds microneedles in an array. Using the process it is possible to reduce costs by using just one chip is used for example in a medical device for drug delivery among other biomedical applications. Because the process can be implemented in a batch there is excellent efficiency, in terms of reduction of processing time, costs and equipment requirements.

Also, because of the manner in which the wet etching timing is controlled, there is very precise control over microneedle dimensions. Because wet etching with alkaline media etches substrates such as silicon along its crystal plane, the resultant microstructures, such as the microneedles, are extremely robust and have smooth surfaces. It is well known that dry etching of silicon microneedles produces a brittle structure which is subject to deformation or breakage when subjected to stresses such as those experienced by the needles when the device is used in medical applications involving insertion into biological tissue. The smooth defect-free surface produced by wet etching, and the robust structure obtained, contribute to the structural and mechanical stability of the wet etched microneedles.

Although the foregoing invention has been described in some detail by way of illustration and example, and with regard to one or more embodiments, for the purposes of clarity of understanding, it is readily apparent to those of ordinary skill in the art in light of the teachings of this invention that certain changes, variations and modifications may be made thereto without departing from the scope of the invention as described in the appended claims. Furthermore the invention is intended to cover not only individual embodiments that have been described but also combinations of the described embodiments.

The invention claimed is:

1. A method of manufacturing a microneedle having a stem and a beveled end, the process comprising:
   providing a semiconductor bulk material having a first and a second face which are parallel to one another;
   depositing a barrier layer on said first and second faces;
   coating said first and second faces with a photolithography sensitive layer;
   removing areas of the photolithography sensitive and barrier layer on the first face to form windows between areas of barrier layer;
   exposing the windows to a wet etching process so part of the semiconductor bulk material is removed from the first face until a cavity is formed having at least one side wall extending at an oblique angle to the first face and towards the second face of the semiconductor bulk material;
   coating the at least one side wall of the cavity with a coating layer;
   forming a channel by dry etching, through the second face of the bulk material towards the coating layer of the cavity so the channel meets the coating layer which provides a cap for the channel as well as capping areas of the semiconductor bulk material that border the channel;

removing the semiconductor bulk material from either side of the cap to leave a capped tube extending from the second face formed from remaining semiconductor bulk material; and removing the cap to form at least one microneedle formed as a stem and beveled end.

2. A method according to claim 1, wherein the semiconductor bulk material is a silicon based material.

3. A method according to claim 1, wherein the barrier layer is an oxide.

4. A method according to claim 3, wherein the oxide is silicon dioxide.

5. A method according to claim 3, wherein the oxide is formed by thermal growth and/or Plasma Enhanced Chemical Vapour Deposition (PECVD).

6. A method according to claim 1, wherein the photolithography sensitive layer is a photoresist.

7. A method according to claim 1, wherein the wet etching process of the windows is a potassium hydroxide wet etch process.

8. A method according to claim 1, wherein the coating layer on the cavity is laid down by physical vapour deposition (PVD) and/or plasma enhanced chemical vapour deposition (PECVD) process.

9. A method according to claim 1, wherein the coating layer on the cavity is laid down by a photolithographic process.

10. A method according to claim 1, wherein the photolithographic process includes spray coating and photolithography.

11. A method according to claim 1, wherein semiconductor bulk material that is either side of the cap is removed using a further wet etch process.

12. A method according to claim 11, wherein the further wet etch process uses a solution of buffered halide, preferably hydrogen fluoride (HF).

13. A method according to claim 1, wherein the dry etch process to form the channels is deep reactive-ion etching (DRIE).

14. A method according to claim 1, wherein the wet etching process is controlled using a series of stop and start processes taking dimensional measurements at each stage.

15. A method according to claim 1, wherein the wet etch time of the wet etch process is balanced based on the dimensions of the cavity and wet etch process temperature.

16. A method according to claim 1, comprising the step of positioning a mask above the coating layer and depositing a further coating onto the area of the coating layer exposed by the mask, and subsequently removing the exposed portion of the coating layer to leave the cap formed of coating layer and further coating.

17. A method according to claim 16, wherein the coating layer is an oxide.

18. A method according to claim 16, wherein the further coating is a metal or metal alloy.

19. A method according to claim 1, wherein the at least one side wall of the cavity comprises a first side wall extending at an oblique angle to the first face and towards the second face of the semiconductor bulk material and at least a second side wall extending at an oblique angle to the first face and towards the second face of the semiconductor bulk material, wherein the first and second side walls converge towards the second face.

* * * * *

UNITED STATES PATENT AND TRADEMARK OFFICE
CERTIFICATE OF CORRECTION

PATENT NO. : 9,919,916 B2  
APPLICATION NO. : 15/031957  
DATED : March 20, 2018  
INVENTOR(S) : Yufei Liu et al.

Page 1 of 1

It is certified that error appears in the above-identified patent and that said Letters Patent is hereby corrected as shown below:

On the Title Page

(72) (Inventors):  
Replace "Yufei Lui, Swansea, (GB)"  
With:  
Yufei Liu, Swansea, (GB)

(73) (Assignee):  
Replace "Semitechnologies Llimited , Swansea, (GB)"  
With:  
Semitechnologies Limited, Swansea, (GB)

Signed and Sealed this  
Eighth Day of January, 2019

Andrei Iancu  
*Director of the United States Patent and Trademark Office*